US008785178B2

(12) United States Patent
Poo et al.

(10) Patent No.: US 8,785,178 B2
(45) Date of Patent: Jul. 22, 2014

(54) PERIFUSION DEVICE

(75) Inventors: Ramon E. Poo, Miami, FL (US);
Camillo Ricordi, Miami, FL (US);
Felipe Echeverri, Miami, FL (US);
Over Cabrera, Deerfield Beach, FL (US); Per-Olof Berggren, Miami, FL (US)

(73) Assignees: Biorep Technologies, Inc., Miami, FL (US); University of Miami, Miami, FL (US)

( * ) Notice: Subject to any disclaimer, the term of this patent is extended or adjusted under 35 U.S.C. 154(b) by 1841 days.

(21) Appl. No.: 11/653,193

(22) Filed: Jan. 12, 2007

(65) Prior Publication Data

US 2008/0168847 A1    Jul. 17, 2008

(51) Int. Cl.
*C12M 3/00* (2006.01)
*C12M 1/16* (2006.01)
*C12M 1/34* (2006.01)
*C12M 1/32* (2006.01)
*C12M 1/00* (2006.01)
*C12M 1/42* (2006.01)
*C12M 1/26* (2006.01)

(52) U.S. Cl.
CPC .............. *C12M 41/36* (2013.01); *C12M 23/12* (2013.01); *C12M 41/14* (2013.01); *C12M 41/00* (2013.01); *C12M 41/46* (2013.01); *C12M 29/10* (2013.01); *C12M 35/04* (2013.01); *C12M 33/10* (2013.01)
USPC ................... 435/286.5; 435/287.3; 435/293.1

(58) Field of Classification Search
USPC ........................................... 435/293.1, 299.1
See application file for complete search history.

(56) References Cited

U.S. PATENT DOCUMENTS

| | | | | |
|---|---|---|---|---|
| 4,650,766 A | * | 3/1987 | Harm et al. | 435/286.6 |
| 4,959,321 A | * | 9/1990 | Preece et al. | 204/604 |
| 5,079,160 A | | 1/1992 | Lacy | |
| 5,424,209 A | * | 6/1995 | Kearney | 435/286.5 |
| 6,416,718 B1 | | 7/2002 | Maiefski et al. | |
| 6,548,263 B1 | | 4/2003 | Kapur et al. | |
| 6,653,124 B1 | | 11/2003 | Freeman | |
| 6,660,149 B1 | * | 12/2003 | Karger et al. | 204/601 |
| 7,323,092 B2 | | 1/2008 | Karger et al. | |
| 2002/0110905 A1 | | 8/2002 | Barbera-Guillem et al. | |
| 2003/0069413 A1 | * | 4/2003 | Pai et al. | 536/25.4 |

OTHER PUBLICATIONS

Cabrera, et al., "Glutamate is an autocrine signal essential for glucagon release." (21 pages).
Cabrera, et al., "Glutamate is a positive autocrine signal for glucagon release," Cell Metabolism (2008) 7: 545: 554.

* cited by examiner

*Primary Examiner* — William H Beisner
(74) *Attorney, Agent, or Firm* — Novak Druce Connolly Bove + Quigg LLP

(57) ABSTRACT

A perifusion device includes at least one sample container for cells, the sample container having an inlet and an outlet. The container receives test liquid through the inlet and discharges the liquid through the outlet. A receptacle housing has a plurality of receptacles for receiving fluid from the outlet of the sample container. A drive is connected to the receptacle housing for moving the receptacle housing such that liquid samples are collected sequentially from the outlet of the sample containers. A computer can be provided to control movement of the receptacle housing at predetermined times, and to record data identifying liquid samples in the receptacles. The test liquid includes at least one stimuli for the cells, which can be the presence, absence, or concentration of a compound in the liquid, or a physical property of the liquid such as temperature. The liquid collected in the receptacles is analyzed to determine the response of the cells to the stimuli.

19 Claims, 19 Drawing Sheets

PERIFUSION DEVICE

BACKGROUND OF THE INVENTION

The response of cells to various stimuli can provide important information about the cells. This information can be useful from a research perspective in discovering and ultimately understanding the reactions of cells to these stimuli. These responses can also have utility in testing the viability and health of the cells. For example, healthy pancreatic islet cells when stimulated with glucose will produce insulin. The rate of production of insulin can provide an indication of the viability of these cells. In order to determine the rate of production, several samples are often taken at intervals and tested for the presence of insulin.

Perifusion is the process of passing a fluid past cells or tissue immersed in the fluid. Apparatus for performing perifusion experiments are usually made from available equipment in the laboratory. The cells are placed into a packed column and inlet and outlet tubing is attached to the column. A solution including the stimuli, such as glucose, is flowed through the column and samples are periodically taken from the column through the outlet and tested for the presence of insulin. The process is time and labor intensive. An attendant must regularly draw and test the samples. In order to provide sufficient data, several samples are usually run simultaneously. In this case, output must be regularly taken from several columns and the samples analyzed for the presence of insulin or whatever products are being measured.

SUMMARY OF THE INVENTION

A perifusion device comprises a sample container. The sample container has a liquid inlet and a liquid outlet, the container receiving liquid through the inlet and discharging through the outlet. A receptacle housing has a plurality of receptacles for receiving fluid from the outlet of the sample container. A drive is connected to the receptacle housing for moving the receptacle housing such that samples from the outlet are collected in the plurality of receptacles. A liquid source can be provided for supplying test liquid to the container.

The perifusion device can further comprise a plurality of sample containers. The plurality of receptacles are positioned in the receptacle housing such that different receptacles receive samples from different liquid outlets of the sample containers. The receptacles can be arranged in rows and columns. The liquid outlets of the sample containers can then be aligned in a row, the rows of receptacles being aligned with the row of liquid outlets to receive samples from the sample containers, such that movement of the receptacle housing by the drive will cause successive receptacles in the columns to receive successive samples from the sample containers. The receptacle housing can be a tray. The tray can have a plurality of receptacles. The receptacles can be in the shape of wells or any other suitable construction.

The sample containers can be columns. The sample containers can be packed with substrate. The substrate can be any suitable substrate, such as beads or gel. The sample container can be constructed so as to permit disassembly, and a portion can be dimensioned to fit within a microcentrifuge tube.

A pump can be provided for causing the test liquid to flow through the column. The pump controls the volumetric flow rate through the sample container. The pump can be a peristaltic pump.

Control means can be provided for operating the drive to move the receptacle housing at predetermined times. The control means is preferably programmable.

At least one sensor can be provided for sensing a characteristic of the fluid. The sensor can be positioned upstream or downstream of the sample, and it is possible to provide sensors both upstream and downstream of the sample.

The cell stimulus can comprise a compound, the compound being at least one selected from the group consisting of carbohydrate, lipid, and peptide. The stimulus can also be any compound in the nature of a drug, which stimulates the behavior of the cells under study in some detectable way.

At least one analytical device can be provided for detecting at least one analyte in the liquid. At least one temperature controller for controlling the temperature of the liquid flowing through the sample container can be provided.

Means for changing the stimulus in a liquid flowing through the sample container can be provided. The means can comprise at least one valve for altering the flow of the stimulus through the sample container. A plurality of valves can be provided, where the valves direct the flow of different test liquids from different liquid sources to a manifold. The manifold directs flow to a sample container.

A method for performing perifusion according to the invention comprises the step of providing a perifusion device. The perifusion device comprises at least one sample container, the sample container having a liquid inlet and a liquid outlet. The container receives liquid through the inlet and discharges the liquid through the outlet. A receptacle housing has a plurality of receptacles for receiving fluid from the outlet of the sample container. A drive is connected to the receptacle housing for moving the receptacle housing such that samples from the outlet are collected in the receptacles.

Cells are placed into the sample container. At least one stimulus for the cells is provided in a test liquid. The test liquid containing the stimulus is caused to flow through the sample container. The liquid is collected from the outlet of the sample container in one of the receptacles. The drive is operated to move the receptacle housing, and at least one additional sample is collected in at least one additional receptacle of the receptacle housing. The response of the cells to the stimulus in the collected samples is then detected.

A method for testing the viability of cells according to the invention comprises the step of placing the cells into a sample container. At least one stimulus for the cells is provided in a test liquid. The test liquid containing the stimulus is caused to flow through the sample container, the stimulus resulting in an indication of cell health that is detectable in liquid leaving the sample container. The liquid is collected from the outlet of the sample container in the receptacles. The response of the cells to the stimulus in the collected samples is then detected and used to determine viability. The method can further comprise the step of determining the number of cells in the sample, which can be used to normalize the data. The number of cells in the sample can be determined by any suitable method, such as measuring the amount of DNA in the sample.

BRIEF DESCRIPTION OF THE DRAWINGS

There are shown in the drawings embodiments which are presently preferred, it being understood, however, that the invention can be embodied in other forms without departing from the spirit or essential attributes thereof.

DETAILED DESCRIPTION OF THE INVENTION

Figure 1:
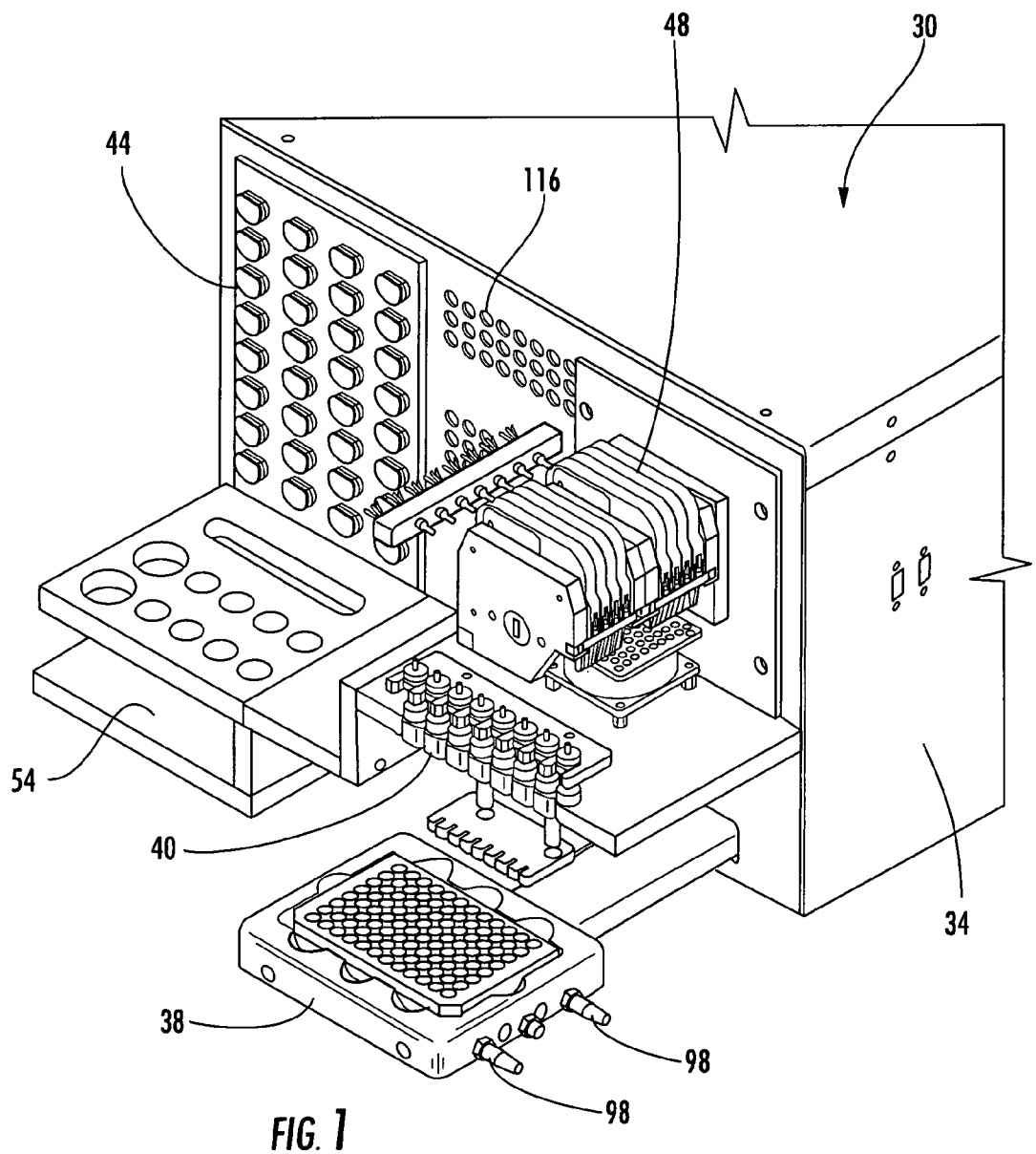
FIG. 1 is a perspective view of a perifusion device according to the invention.
Figure 2:
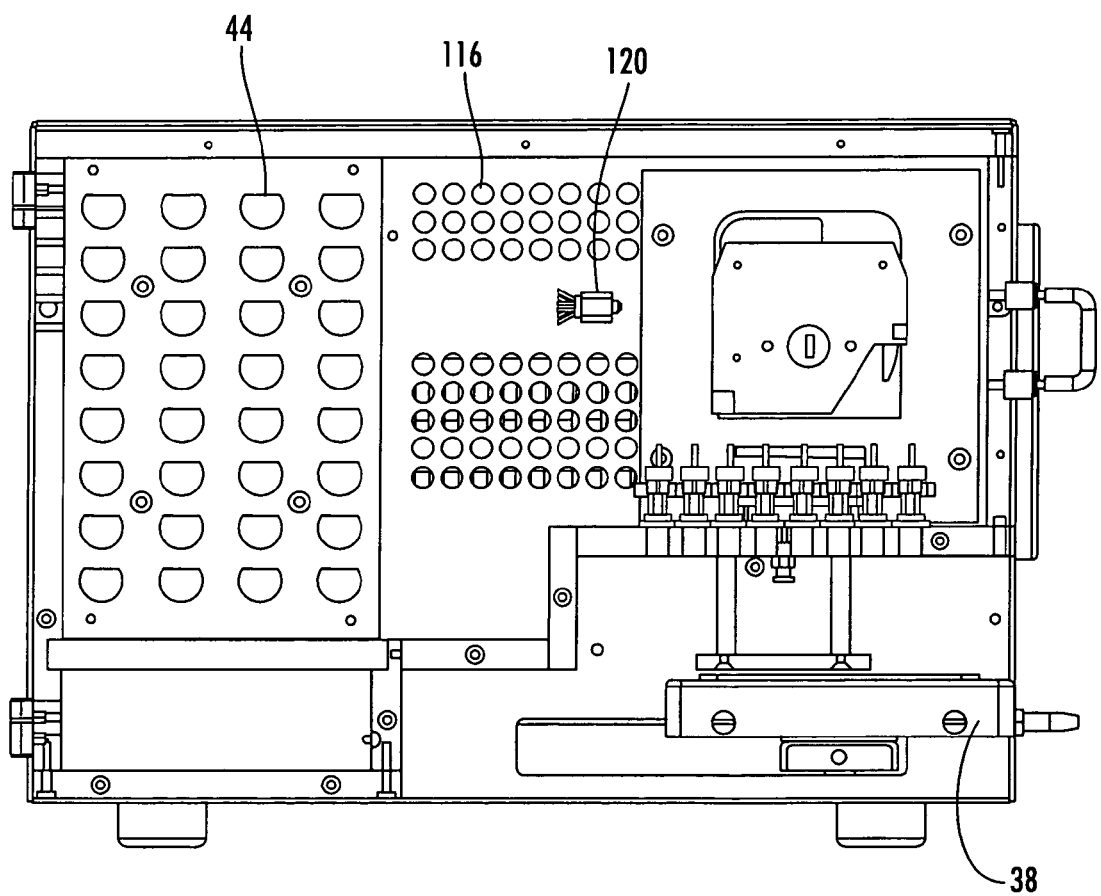
FIG. 2 is a front elevation.
Figure 3:
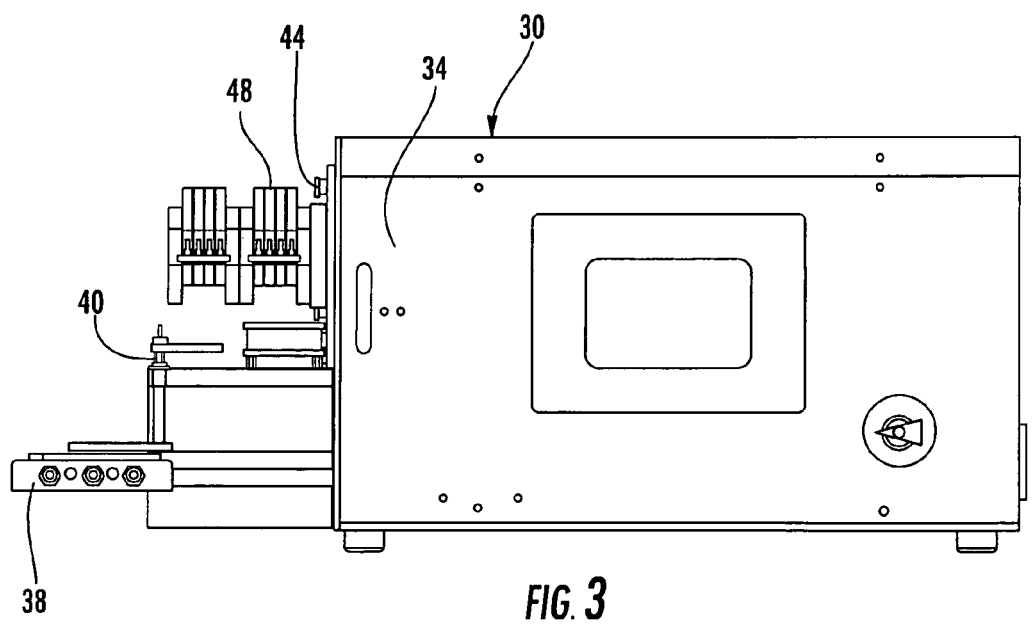
FIG. 3 is a right side elevation.
Figure 4:
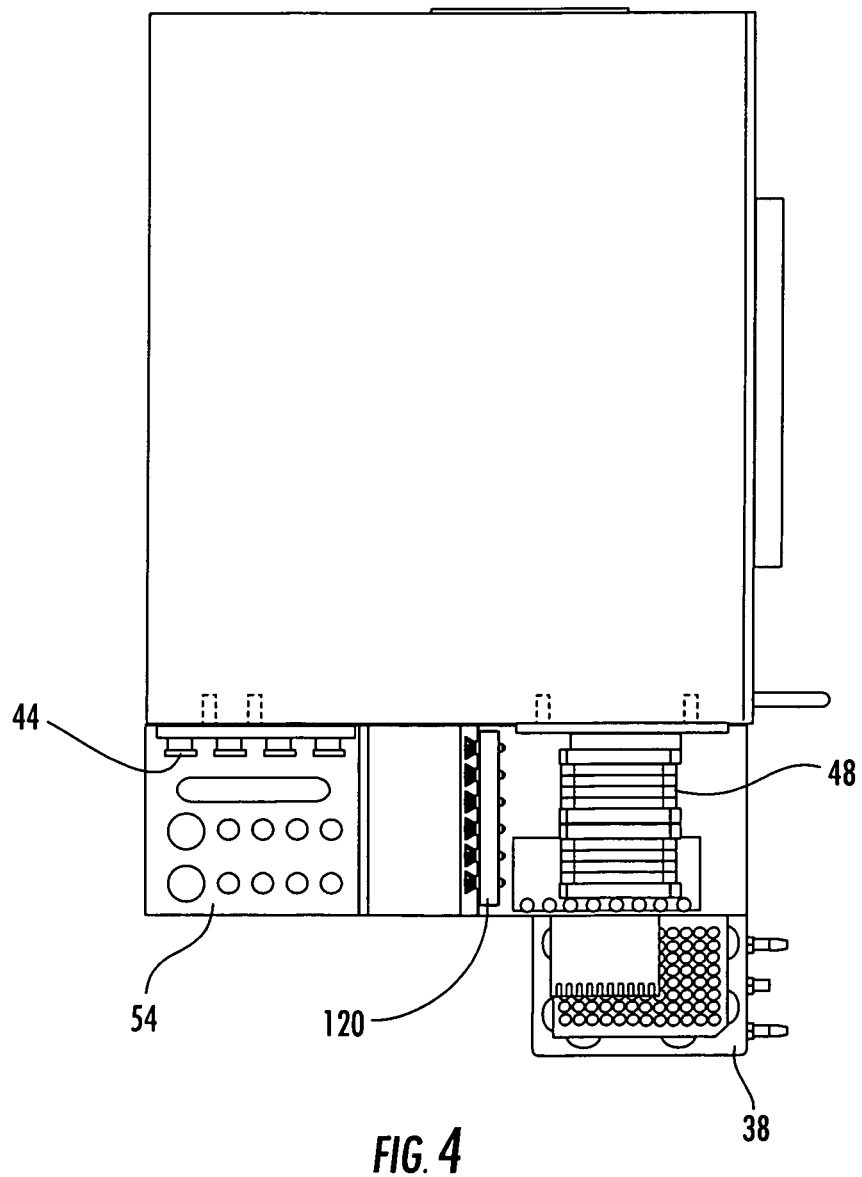
FIG. 4 is a top plan view.
Figure 5:
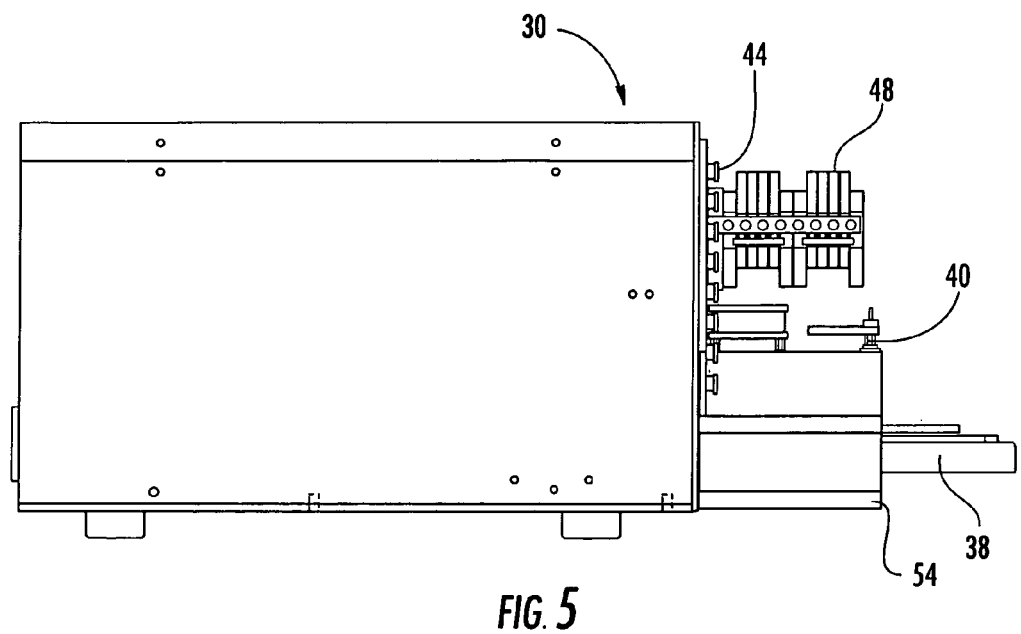
FIG. 5 is a left side elevation.

There is shown in FIG. 1 a perifusion device 30. The perifusion device 30 has a housing 34 and a receptacle housing 38. A plurality of sample containers 40 are mounted generally above the receptacle housing 38. A plurality of valves 44 are used to control the flow of test liquids and compounds from source containers to the sample containers 40. Suitable pumping apparatus such as pump assembly 48 is provided to control the flow of solution through the sample containers 40. Flow from the source containers is controlled by suitable structure such as the valves 44 and the pump 48 to direct solutions through the sample containers 40. Several different pump/valve constructions and designs can be utilized. Samples are collected at the receptacle housing 38 and can be analyzed separately. The dynamic response of cell samples in the sample containers 40 to stimuli in the solutions from the solution containers is measured.

The solution containers can be of any suitable construction, and can be provided separately or connected to the perifusion device 30. Source containers 50 can be supported on a rack 54 or other suitable supports. Solution can be routed from the source containers 50 through suitable conduits such as flexible tubing. Other source containers or solution sources are possible.

Figure 6:
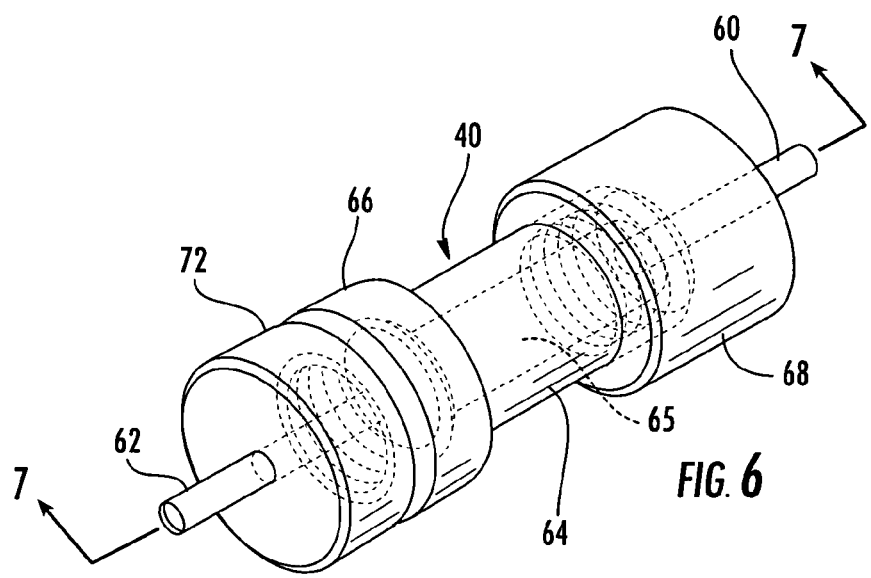
FIG. 6 is perspective view, partially in phantom, of a sample container.
Figure 7:
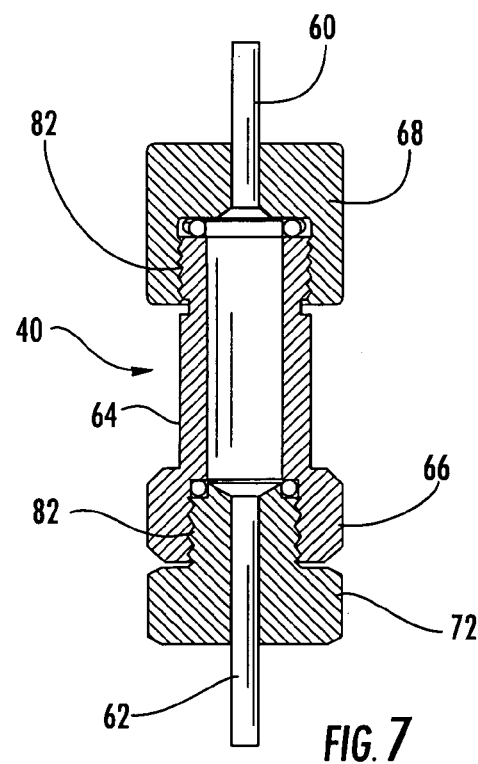
FIG. 7 is a cross section taken along lines 7-7 in FIG. 6.
Figure 8:
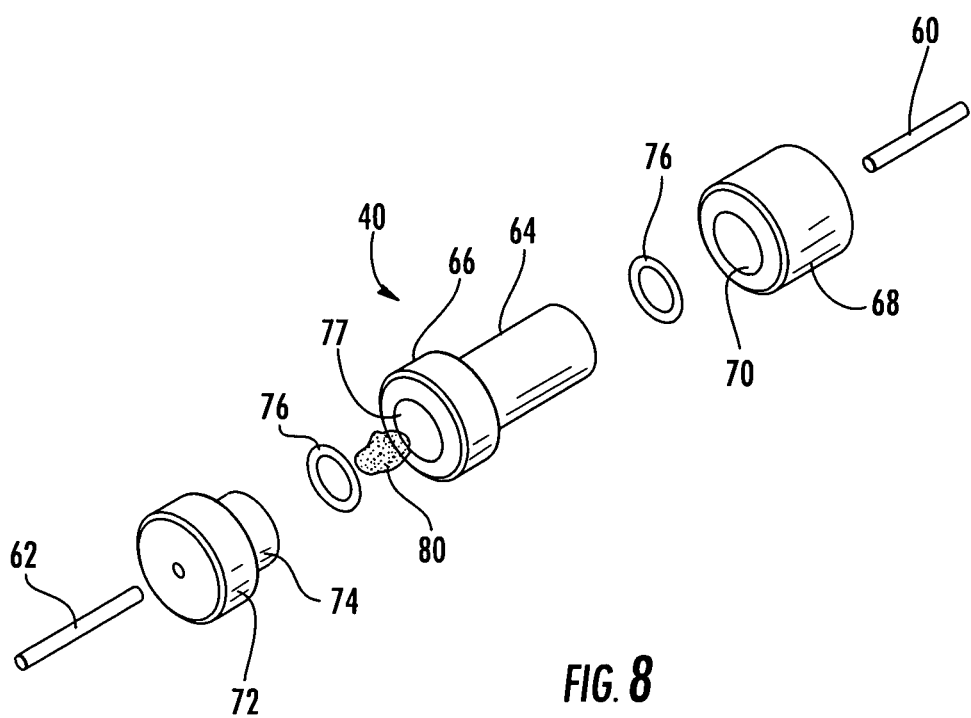
FIG. 8 is an exploded perspective view of a sample container.

A sample container 40 is illustrated in FIGS. 6-8. The sample container 40 can be of any suitable size or construction. In general, the sample container 40 will have an open interior for placement of the sample and will have an inlet 60 and an outlet 62, whereby test fluids can flow into the sample container 40 through the inlet 60, contact the sample, and exit from the sample container 40 through the outlet 62. The sample container 40 can include a main body portion 64 which has an open interior 65. A collar 66 can be provided and has a diameter that is greater than that of the main body portion 64. End cap 68 has an opening 70 adapted to receive an end of the main body portion 64. Inlet 60 is positioned through a suitable opening in the end cap 68. A second end cap 72 has a neck 74 adapted to fit within an opening 77 in collar 66 of main body portion 64. Outlet 62 is positioned within a suitable opening within the second end cap 72. Suitable sealing structures such as o-rings 76 can be provided. The sample 80 is positioned within the open interior 65 of the main body portion 64 and end caps 68 and 72 are secured. Cooperating threads 82 can be used to secure the caps 68, 72 to the main body portion 64.

The valves 40 can be of any suitable construction. In one aspect, the valves 40 are pinch valves which perform the valve function by selectively applying pressure to flexible conduits so as to close the conduit to fluid flow, and then releasing that pressure to permit flow. Other valve and conduit constructions and arrangements are possible.

Figure 10:
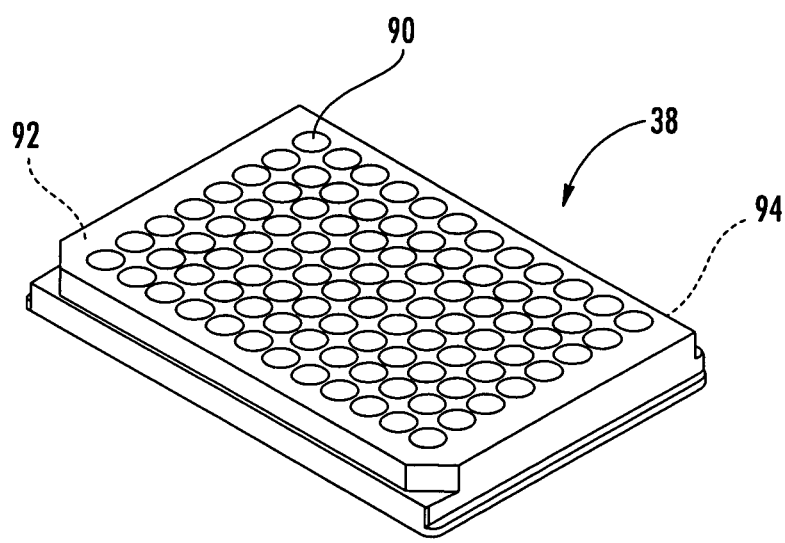
FIG. 10 is a perspective view of a receptacle housing.
Figure 11:
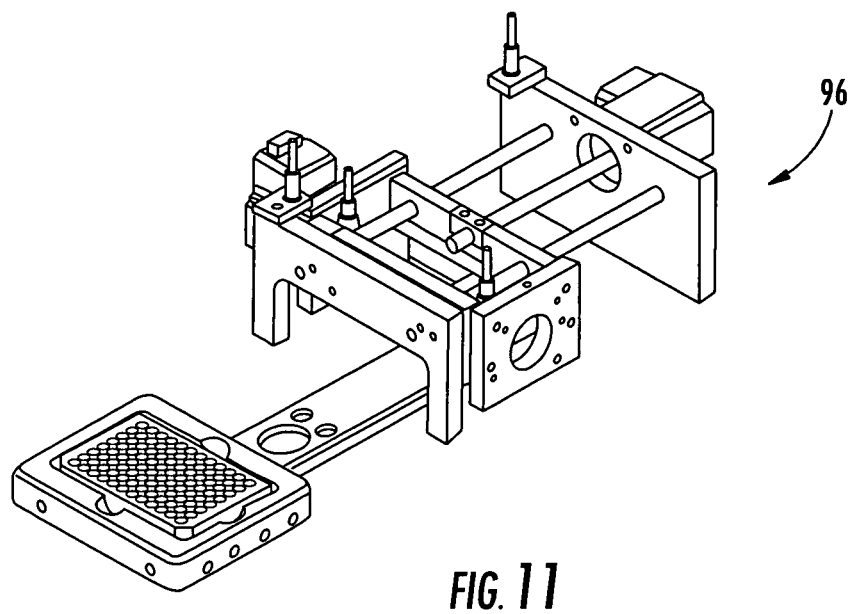
FIG. 11 is a perspective view of a receptacle drive assembly.
Figures 12, 13:
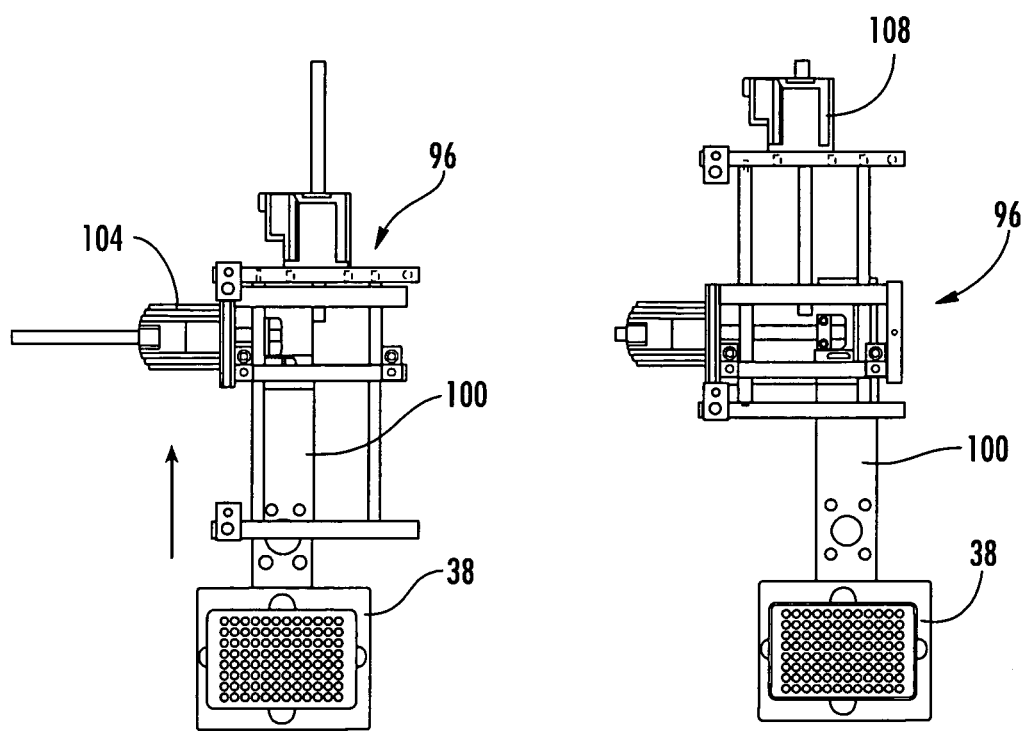
FIG. 12 is a top plan view in a first mode of operation.
FIG. 13 is a top plan view in a second mode of operation.
Figure 14:
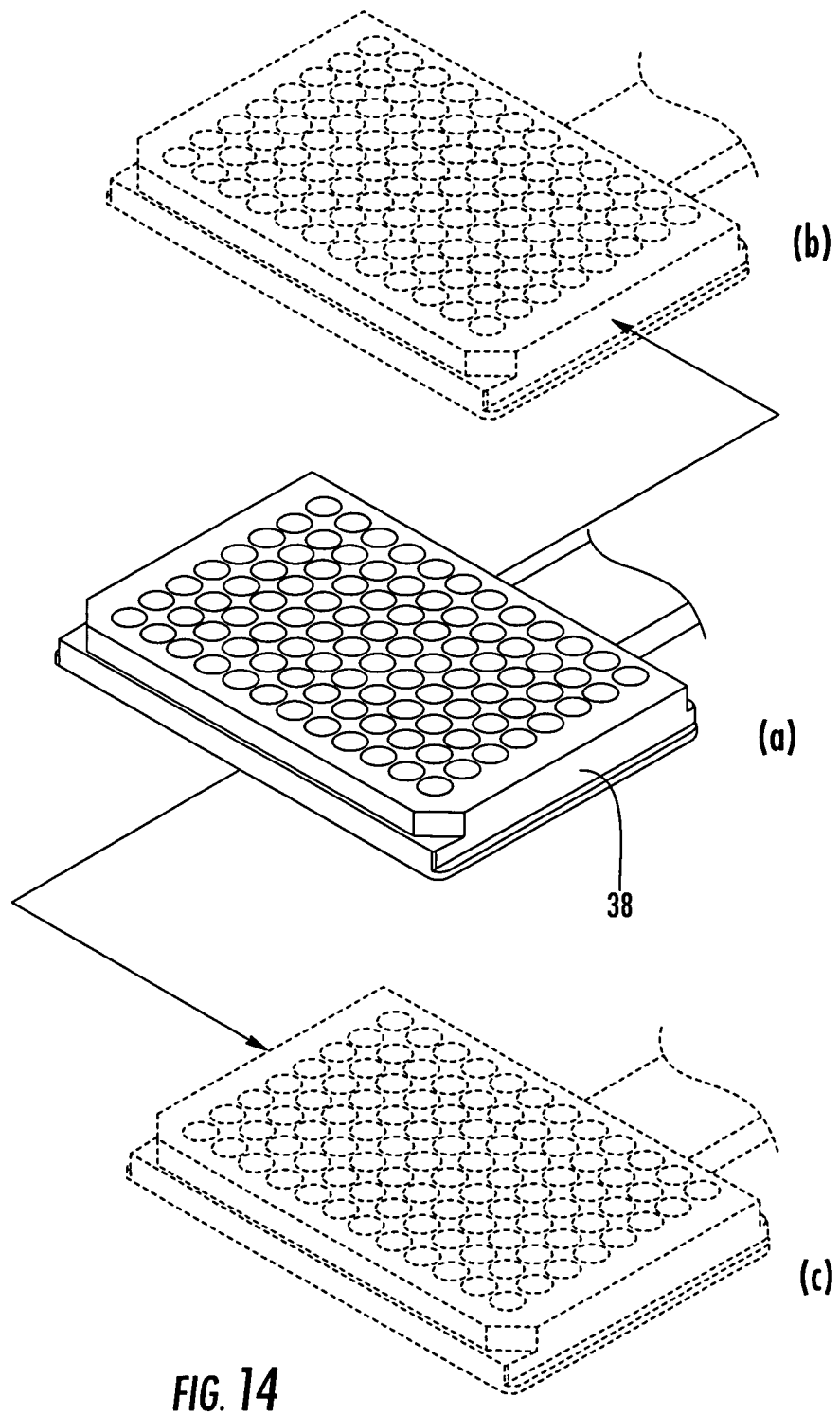
FIG. 14(a-c) is a perspective view, partially in phantom, of a receptacle housing in various modes of operation.

The receptacle housing 38 can also be of any suitable shape. As shown in FIG. 10, the receptacle housing can be a tray having a plurality of suitable receptacles such as wells 90 arranged in rows 92 and columns 94. The receptacle housing 38 is mounted to a drive assembly 96 (FIGS. 11-13) which is capable of incrementally moving the receptacle housing such that wells 90 are sequentially moved to a position to receive subsequent samples from a sample container 40. The receptacle housing can be connected to a drive arm 100 which is in turn connected to a suitable drive assembly. In one aspect, the drive assembly can include a motor 104 for moving the arm to and away from the drive assembly, and a motor 108 for moving the receptacle housing 38 transversely (FIGS. 12-13). Motors 104 and 108 can be operated to move the arm 100 both axially and transversely to position the wells 90 to receive samples from the sample containers 40. The manner in which the receptacle housing 38 is moved, whether axially, transversely or both, can be varied so long as data is maintained as to which well 90 received a sample from which sample container 40 at a given time. Thus the receptacle housing 38 can be moved from the position (a) in FIG. 14, both axially and laterally to the position (b). The receptacle housing 38 can alternatively be moved axially outward and transversely in a different direction to the position (c). Structure can be provided to permit the control of temperature in the receptacle housing 38. Such structure can include heating/cooling channels which receive heating/cooling fluid through fluid connection ports 98.

Figure 15:
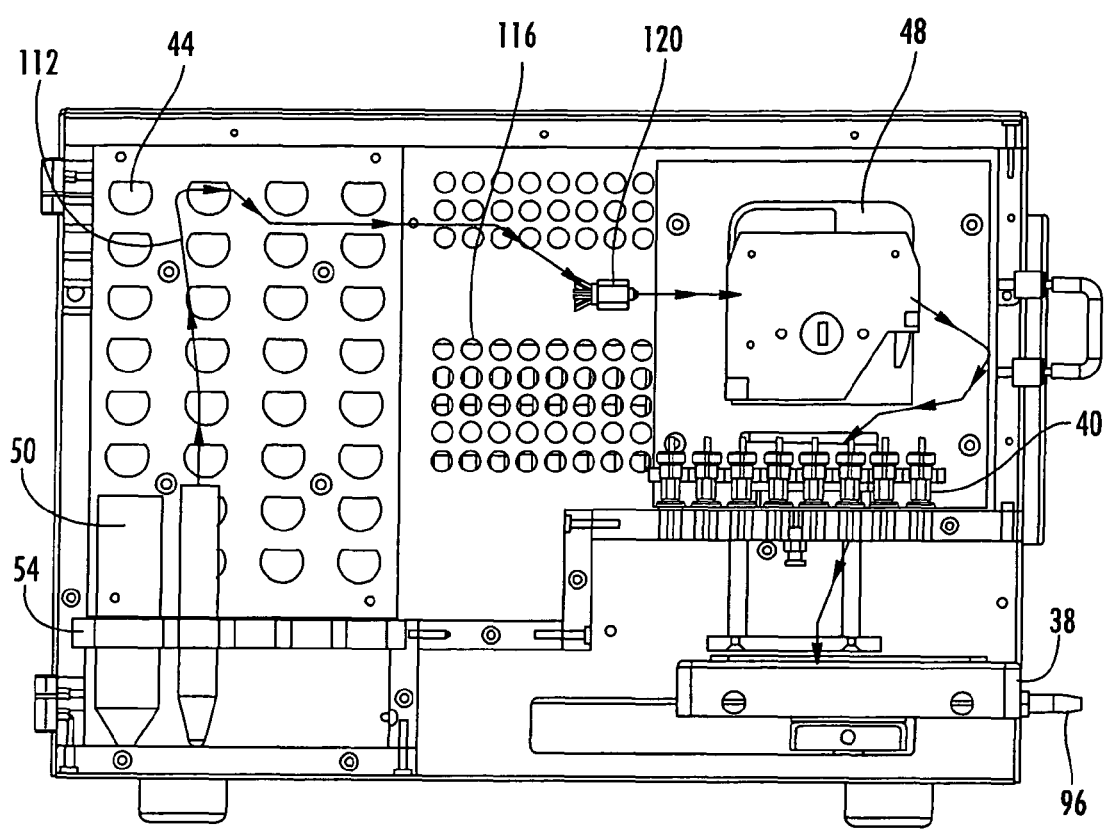
FIG. 15 is a front elevation of a perifusion device illustrating a fluid flow path through the device.
Figure 16:
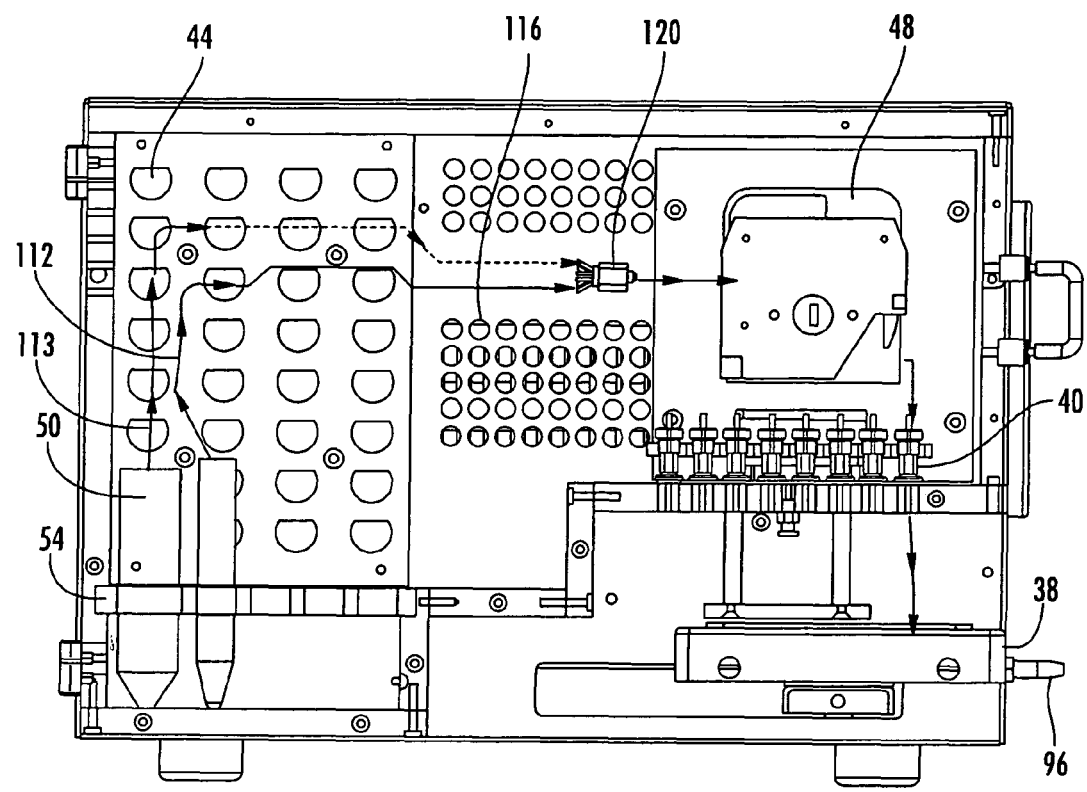
FIG. 16 is a front elevation of a perifusion device illustrating alternative fluid flow paths through the device.
Figure 17:
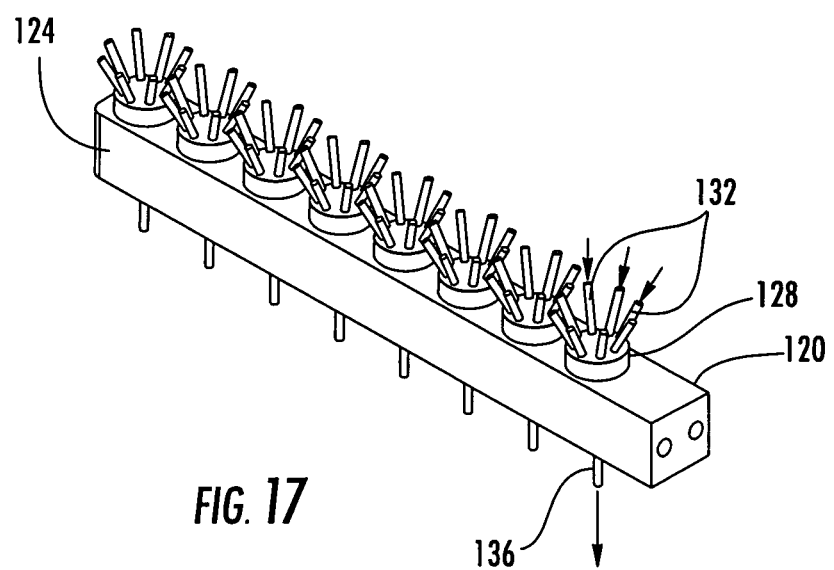
FIG. 17 is a perspective view of a manifold assembly.

Fluid flow through the perifusion device 30 is illustrated in FIGS. 15-16. Fluid from the source containers 50 flows through suitable conduit structure in the direction shown by path 112 past valves 44 to the pump 48. Fluid then flows to the sample containers 40, and through the outlet of the sample container 40 to a well 90 in a receptacle housing 38. Temperature control of fluid in the conduit can be provided by any suitable structure, such as vented heating/cooling air which flows through outlet ports 116 to contact the conduit. Operation of valves 44 can prevent test solution from flowing through path 113 to reach the sample container (FIG. 16), and then the valves 44 can be operated to prevent solution from flowing through path 112.

Figure 9:
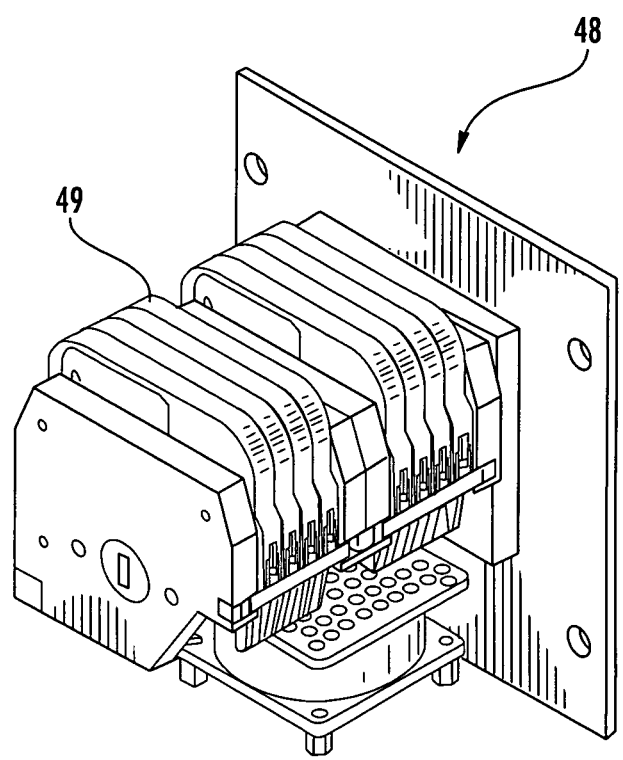
FIG. 9 is a perspective view of a pump assembly.

The pump 48 can be of any suitable construction. In one aspect, the pump 48 is a peristaltic pump having eight channels 49 (FIG. 9). The peristaltic pump preserves sterility by applying pressure through rotating arms to pinch a flexible conduit against a curved surface and thereby move the fluid within the conduit. The pump can have multiple channel 49, whereby a single drive motor can operate separate sets of rollers which operate to pump fluid through separate fluid conduits positioned in the channels. In the illustrated embodiment, the peristaltic pump 48 had eight fluid channel 49, permitting the pumping of fluid through eight distinct conduits. However, more of fewer channels are possible. Also, pumping devices other than peristaltic pumps is possible.

It is possible to have any number of sample containers 40. In the illustrated embodiment, eight sample containers 40 are provided. Different source containers 50 will typically have different solutions for testing samples within the sample containers 40. Also, different testing protocols may be desired for different samples within the sample containers 40. Accordingly, it is desirable to provide flow paths such that solution from one source container 50 can be routed to more than one sample container 40, either simultaneously or sequentially. In the illustrated embodiment, a manifold assembly 120 is provided (FIG. 16). The manifold assembly 120 has support structure 124 and a plurality of individual manifolds 128. Each manifold 128 has a plurality of inlet ports 132, connecting to a single outlet port 136. Any number of inlet ports 132 are possible. In the illustrated embodiment, there are eight inlet ports 132. Operation of the valves 44 permits fluid to flow through one of the ports 132 and the outlet port 136 so as to permit fluid flow therebetween. The remaining inlet ports 132 are closed by operation of valves 44 on the respective conduits connecting to the other ports 132 such that fluid flow through these inlet ports is prevented. It will be appreciated that by use of multiple flow paths from each source container 50, where each flow path is separately controlled by a valve 44, and connects to a manifold 128, that fluid flow from various ones of the source containers 50 to various ones of the sample containers 40 is possible. This permits the control of experiments, whereby differing solutions can be flowed through differing sample containers 40 at different times according to the experimental design.

Computer control can be provided to operate the perifusion device 30. This control can be utilized to operate, among other things, the valves 44, pump 48, and position of the receptacle housing 38 through control of the motors 104, 108. Also, the computer can have internal data storage or can connect to such data storage in order to record the position of the receptacle housing with time such that a record is kept as to the particular samples which were collected in particular receptacles 90 of the receptacle housing 38. Computer control can also control flow rates and temperature, as well as switching of solutions with time according to the experimental design.

Samples are placed within the sample containers 40. The cells will sometimes agglomerate within the sample container 40 during the experiment. The cells can be immobilized within the sample containers 40 by suitable means such as support beads, a gel immobilizer, or other cell immobilizing methods. The beads or gel will separate and support the cells within the container. Solutions are provided in source containers 50 and tubing is connected between the source containers 50, the valves 44, and the sample containers 40. Other systems for providing solutions to the sample containers 40 are possible. The pump 48 is operated to cause the solutions to flow through the sample containers 40. The pump 48 can be manipulated to control the volume flow rate through the sample containers, and can be used to vary this rate if desired for purposes of changing the behavior of the cells. The flow of the solution stimulates the cells to change their behavior.

The test solution can be any solution which will stimulate a change in cell behavior. The stimulus can be the presence, absence or concentration of one or more compounds in the test liquid, or a property of the liquid. The compound can be a carbohydrate, lipid or peptide. The compound can be in the nature of a drug, which stimulates cell behavior in some detectable way. In the case of pancreatic islet cells, the solution can be a glucose solution, or a series of glucose solutions having differing concentrations, or other known insulin stimulants such as GLP-1 or KCl. In other cases, the solution can contain various drugs or substances which effect some change in cell behavior, such as compounds which block cellular receptors. The sample fluid could alternatively contain some substance which is removed by the cells, whereby the extent of removal can provide information about the cells. The stimulus can also be some physical property of the solution, such as temperature or pH.

The system is dynamic as the solutions can be changed with time, such as by changing the concentration of a stimulant or changing the stimulant itself, by switching between source containers 50. Such dynamic characteristics can be used in the case of islet cells to simulate a meal, for example. The receptacle housing 38 is moved to collect samples in wells 90. It is alternatively possible to move the sample containers 40 rather than the receptacle housing 38, so long as they move relative to one another, but movement of the sample containers could change the dynamics of the system by altering cell state within the sample container. Movement of the receptacle housing 38 is controlled such that samples taken from the sample containers can be identified. The samples are then analyzed to detect the change in behavior of the cells. A robot can be used to automatically remove the receptacle housing 38 in order to improve the throughput of the device.

Figure 18:
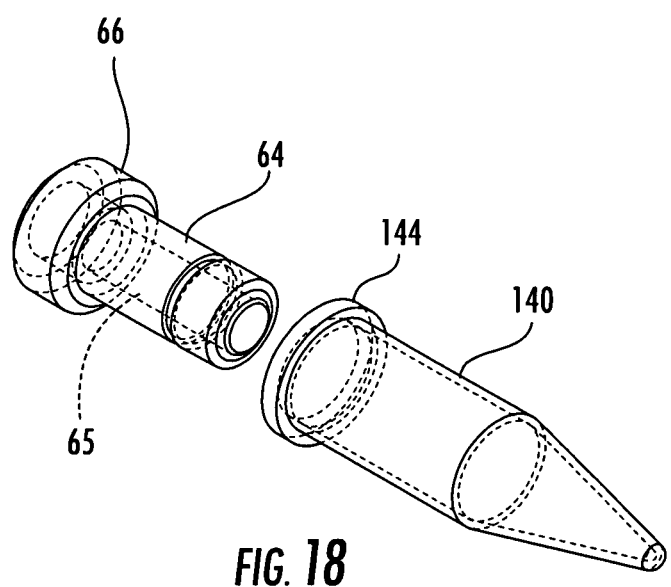
FIG. 18 is an exploded perspective view, partially in phantom, of a portion of a sample container and a microcentrifuge tube.
Figure 19:
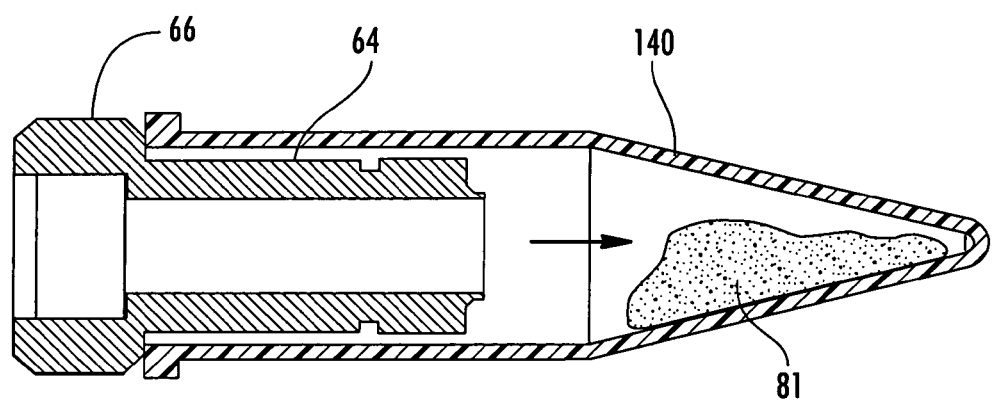
FIG. 19 is a cross section illustrating a portion of a sample container and a sample in a microcentrifuge tube.

Following an experiment, the fluid collected in the wells 90 is analyzed. The method of analysis will depend on the experiment and the characteristics of the fluid sample that are to be determined. Suitable analysis methods can include high speed liquid chromatography, mass spectrometry, and the like. It is also possible to provide one or more sensors in the fluid flow path to analyze such characteristics as oxygen content, pH, turbidity, and others. Such sensors can be provided upstream and downstream from the cell samples so as to detect changes in these characteristics and thereby cell behavior. The cells within the sample containers 40 can also be removed and analyzed. Removal can be accomplished by disconnecting the end cap 68 and 72. The main body portion 64 with the sample within the open interior 65 is then removed. The main body portion 64 is dimensioned to fit within a micro centrifuge tube 140 with the collar 66 seated against lip 144 of the micro centrifuge tube (FIGS. 18-19). In this manner, the sample 81 can be rapidly removed and centrifuged for analysis of the sample 81. The analysis of the cells can be by known techniques. The number of cells in the sample can also be determined to normalize the results of testing for differing numbers of cells in the samples. The number of cells can be ascertained by any suitable method, such as from the amount of DNA in the sample.

Figure 20:
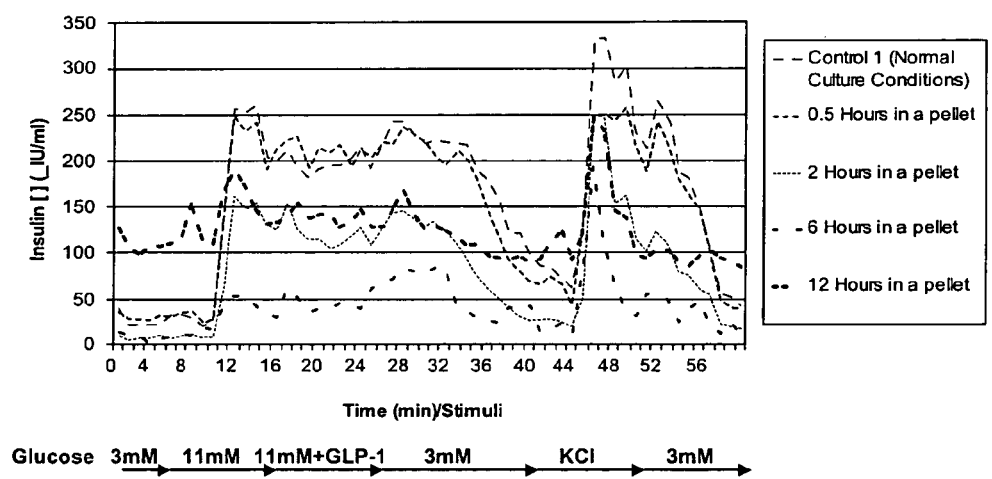
FIG. 20 is a graph of insulin release versus time from stimuli after anoxic conditions.
Figure 21:
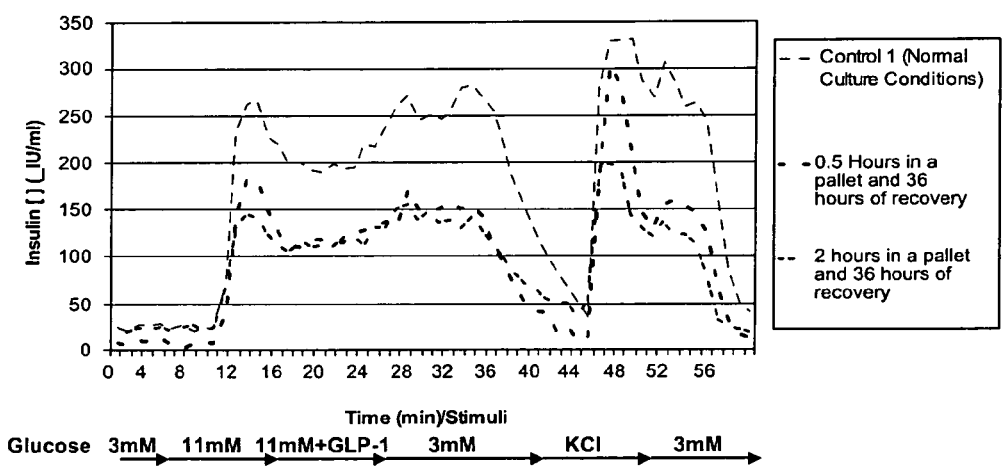
FIG. 21 is a graph of insulin release versus time from stimuli after anoxic conditions and 36 hours recovery time.
Figure 22:
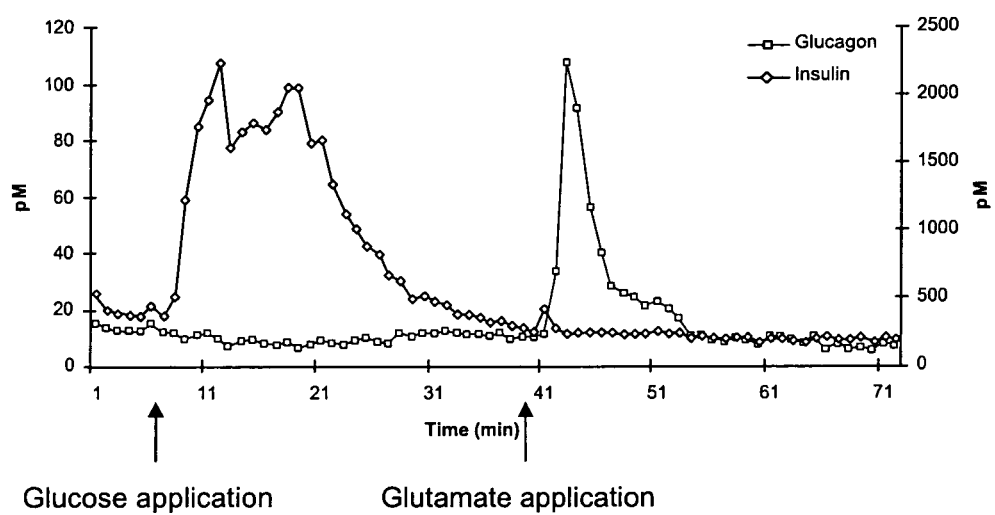
FIG. 22 is a graph of glucagon/insulin release versus time.

FIGS. 20-22 illustrate experimental results using the perifusion device 30 according to the invention. FIG. 20 illustrates insulin release by perifusion with time. Islet cells were compromised by depriving them from the normal oxygen concentration for 0.5, 2, 6 , and 12 hours. After that, these islets were incubated in the perifusion system and exposed to substances that stimulate insulin release such as 11 mM of glucose, GLP-1 in addition to 11 mM of glucose, and potassium chloride (KCl). The profile of insulin release measured by ELISA of the samples collected from the perifusion system indicates that islets responded to the stimuli in a way that is proportional to the health of the islets. The control batch, normal culture conditions without oxygen deprivation, showed a prominent response to all three stimuli. Two and six hours of oxygen deprivation diminished the response in agreement with the time these cells were incubated with low oxygen. In the case of twelve hours of incubation with low oxygen, the health of the islets seem to be irreversibly compromised. The cells had little or no response to 11 mM glucose and GLP-1, and the KCl response was very small. These cells are constantly secreting insulin in a non-regulated fashion, as shown by the passive release at 3 mM glucose. This may indicate that this batch of islets is severely damaged.

FIG. 21 illustrates insulin released by perifute in which pancreatic cells were deprived from oxygen but their ability to secrete insulin in response to stimuli was not tested until thirty-six hours after they had been removed from the anoxic conditions (recovery time). Again, an insulin release assay using the perifusion system is indicative of the health of the islets. Even though these islets were allowed to recover from the anoxic trauma, their insulin release profile indicates that their potency had been diminished by the adverse conditions to which they were exposed (low oxygen). Therefore, the perfusion assay not only can provide information about the current status of the islets, but also can give clues about past traumatic conditions and how much these conditions affected the islets. Six and twelve hours of oxygen deprivation was so traumatic to the islets that the majority of these cells died and could not be assayed after thirty-six hours.

FIG. 22 illustrates glucagon-insulin release from in vitro perifused human islets. This experiment was conducted to show the usefulness of the perifusion system in drug screening. Insulin and glucagon are hormones secreted from the beta and alpha cells of the islets of Langerhans. The release profile was measured in the perifusion system after stimulation with glucose which stimulated the beta cells to release insulin and kainates which stimulated the alpha cells to produce glucagon. The figure demonstrates a very prominent and clean release profile for each compound. In the same way, any other compound's ability to influence the health or alter the behavior of the pancreatic islets can be assayed using the perifusion system of the invention.

This invention can be embodied in other forms without departing from the spirit or essential attributes thereof and, accordingly, reference should be had to the following claims rather than the foregoing specification as indicating the scope of the invention.

We claim:

1. A perifusion device, comprising:
   a plurality of sample containers;
   the sample containers having a liquid inlet and a liquid outlet, the containers receiving liquid through the inlet and discharging liquid through the outlet;
   a plurality of liquid sources for supplying a plurality of liquids to said sample containers;
   a plurality of manifolds disposed between the liquid sources and the sample containers, each manifold having a plurality of manifold inlets and at least one manifold outlet, each liquid source being in fluid connection to at least one manifold inlet, each manifold outlet being in fluid communication with a plurality of manifold inlets, each manifold outlet being in fluid connection with a liquid inlet of a sample container;
   a plurality of valves, said valves controlling liquid flow from the liquid sources through the manifold inlets;
   at least one pump for pumping liquid from the manifold outlets to respective sample containers;
   a receptacle housing having a plurality of receptacles for receiving fluid from the liquid outlets of the sample containers, said plurality of receptacles being positioned in said receptacle housing such that different receptacles receive samples from different liquid outlets of each of said sample containers;
   a drive connected to the receptacle housing for moving said receptacle housing such that samples from the outlet are collected in said plurality of receptacles; and,
   a programmable controller that is programmed to operate the driver to move the receptacles at predetermined times, to operate the valves, and to record the position of the valves and the receptacles as a function of time so as to correlate the liquids that are supplied to each sample container from the plurality of liquid sources with the liquid samples that are received by the receptacles from the sample containers.

2. The perifusion device of claim 1, wherein said receptacles are arranged in rows and columns.

3. The perifusion device of claim 2, wherein said liquid outlets of said sample containers are aligned in a row, said rows of receptacles being aligned with said row of liquid outlets to receive samples from said sample containers, and whereby movement of said receptacle housing by said drive will cause successive receptacles in said columns to receive successive samples from said sample containers.

4. The perifusion device of claim 3, wherein said receptacles are wells.

5. The perifusion device of claim 1, wherein said sample containers are columns.

6. The perifusion device of claim 1, wherein said sample containers are packed with substrate.

7. The perifusion device of claim 6, wherein said substrate comprises at least one selected from the group consisting of beads and gel.

8. The perifusion device of claim 1, wherein said pump controls the volumetric flow rate through said container.

9. The perifusion device of claim 1, wherein said pump is a peristaltic pump.

10. The perifusion device of claim 1, further comprising at least one sensor for sensing a characteristic of the fluid.

11. The perifusion device of claim 1, comprising at least one sensor upstream of the sample and at least one sensor downstream of the sample.

12. The perifusion device of claim 1, wherein at least one of said liquid sources comprises a cell stimulus compound, said compound being at least one selected from the group consisting of carbohydrate, lipid, and peptide.

13. The perifusion device of claim 1, wherein at least one of said liquid sources comprises a cell stimulus compound, said cell stimulus compound comprising a drug which stimulates cell behavior in some detectable way.

14. The perifusion device of claim 1, wherein said receptacle housing is a tray.

15. The perifusion device of claim 14, wherein said tray comprises a plurality of receptacles.

16. The perifusion device of claim 1, further comprising at least one analytical device for detecting at least one analyte in said liquid.

17. The perifusion device of claim 1, further comprising at least one temperature controller for controlling the temperature of said liquid flowing through said sample container.

18. The perifusion device of claim 1, wherein said plurality of valves control flow of different test liquids to different ones of said manifold inlets that are in fluid communication with the same manifold outlet, said manifold outlets directing flow to one of said sample containers.

19. The perifusion device of claim 1, wherein said sample container comprises a main body portion and a collar, said main body portion dimensioned to fit within a microcentrifuge tube, said collar dimensioned to abut an end of the microcentrifuge tube.

* * * * *